United States Patent [19]
Dittrich

[11] Patent Number: 4,554,270
[45] Date of Patent: Nov. 19, 1985

[54] PESTICIDAL COMPOSITION CONTAINING A SYNERGISTIC COMBINATION OF 3-HYDROXYMETHYLACRYLIC ACID METHYL ESTER DIMETHYLTHIONOPHOSPHATE AND CYPERMETHRIN

[75] Inventor: Volker Dittrich, Zeiningen, Switzerland

[73] Assignee: Ciba Geigy Corporation, Ardsley, N.Y.

[21] Appl. No.: 672,049

[22] Filed: Nov. 16, 1984

Related U.S. Application Data

[62] Division of Ser. No. 500,491, Jun. 2, 1983, Pat. No. 4,500,521.

[30] Foreign Application Priority Data

Jun. 7, 1982 [CH] Switzerland ............... 3505/82

[51] Int. Cl.$^4$ ............................................. A01N 57/00
[52] U.S. Cl. .................................................. 514/120
[58] Field of Search .......................... 424/212; 514/120

[56] References Cited

U.S. PATENT DOCUMENTS 4,017,611 4/1977 Beriger et al. ..................... 424/212
4,308,262 12/1981 Badmin et al. ..................... 424/200

Primary Examiner—Allen J. Robinson
Attorney, Agent, or Firm—Edward McC. Roberts; Frederick H. Rabin; Bruce M. Collins

[57] ABSTRACT

A novel pesticidal composition containing the synergistically effective active-substance combination comprising the compound: S-[6-chloro-oxazolo[4,5-b]-pyridin-2(3H)-on-3-yl-methyl]-O,O-dimethyl-thiophosphate or the compound: $(CH_3O)_2P(S)—OCH=C(CH_3)—C(O)OCH_3$ with the compound: 1(RS)-cis,trans-3-(2,2-dichlorovinyl)-2,2-dimethyl-cyclopropanecarboxylic acid-(RS)-($\alpha$-cyano-3-phenoxybenzyl) ester.

The compositions are used for the control of various pests. They are suitable in particular for controlling stored-food pests, granary pests and other storehouse pests of the orders:

Coleoptera, Lepidoptera and Acarina. Also hygiene pests of the orders: Diptera and Blattaria can be successfully controlled with these compositions.

2 Claims, No Drawings

PESTICIDAL COMPOSITION CONTAINING A SYNERGISTIC COMBINATION OF 3-HYDROXYMETHYLACRYLIC ACID METHYL ESTER DIMETHYLTHIONOPHOSPHATE AND CYPERMETHRIN

This is a division of application Ser. No. 500,491 filed June 2, 1983, now U.S. Pat. No. 4,500,521 issued Feb. 19, 1985.

The present invention relates to a novel pesticidal composition containing as active ingredient an active substance combination, to the use thereof for controlling pests, especially insects, and also members of the order Acarina, and to the production of this composition.

The control of pests is now becoming increasingly difficult. Factors playing a significant part in this connection are on the one hand the build-up of resistance which the pests to be controlled exhibit against the pesticidal compositions being used, and on the other hand the contamination of the environment caused by the necessary increase of the applied concentrations of active substances. A reduction in the employed amounts of chemical substances must therefore be aimed at in order to avoid the disadvantageous consequences for the environment. However, the emergence of resistant species of pests is promoted by the use of lower active-substance concentrations which offer no guarantee of a complete destruction of the pest populations, including the development stages thereof.

To avoid these disadvantages, it is thus desirable for the control of pests, such as insects and Acarina, to provide compositions which are sufficiently effective even in small applied amounts, and which neither promote the development of resistance nor constitute a danger with respect to the contamination of the environment. Attempts have hence frequently been made to satisfy these requirements by the use of a combination of different substances for the purpose of utilising the potentiation effects thereby occurring. Mixtures of compounds from various classes of substances, for example pyrethrins, pyrethroids, carbamates and phosphoric acid esters, have already been described as synergistically effective preparations in the pesticidal field. It has however been shown that the known combination preparations do not in every case fulfill to the desired extent the demands made of them in practice, particularly with regard to effectiveness, toxicity and economy in application.

There has now been found a novel synergistically acting combination consisting either of the compound: S-[6-chloro-oxazolo[4,5-b]pyridin-2(3H)-on-3-yl-methyl]-O,O-dimethyl-thiophosphate of the formula I

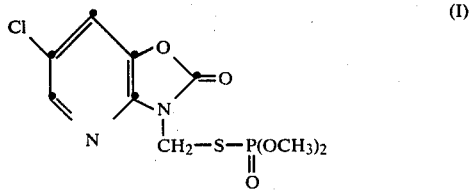

or of the compound: $(CH_3O)_2P(S)-OCH=C(CH_3)-C(O)OCH_3$ of the formula II

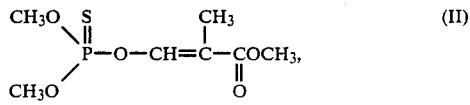

and the compound: 1(RS)-cis,trans-3-(2,2-dichlorovinyl)-2,2-dimethyl-cyclopropanecarboxylic acid-(RS)-(α-cyano-3-phenoxybenzyl)ester of the formula III

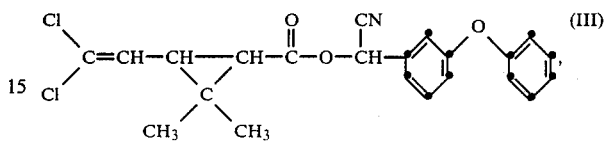

which combination exhibits a broad spectrum of biocidal activity, and which can be incorporated for use into novel compositions according to the invention.

The substance of the formula III is a mixture of cis and trans isomers, and the ratio of cis to trans forms can be high or low.

The active-substance combination according to the invention is used for the control of various pests. It is suitable in particular for controlling stored-food pests, granary pests and other storehouse pests of the orders: Coleoptera, Lepidoptera and Acarina. Also hygiene pests of the orders of Diptera and Blattaria can be successfully controlled.

The individual components of the active-substance combination according to the invention are known as pesticides, and can be produced by known methods. The compounds of the formulae I and II are described in the German Auslegeschriften Nos. 2,131,734 and 2,119,488, and are known under the designations of Alfacron ® and Damfin ®, respectively, whilst the compound of the formula III is published under the name of Cypermethrin in the Pesticide Manual, 6th Edition, 1979.

The range of 5000:1 to 1:1 applies with regard to the determining weight ratios of the compounds I to III in the compositions according to the invention. The combination ratio in the range of 1500:1 to 1:1 is especially suitable for inducing the synergistic effect, and within these limits, the range of 300:1 to 1:1 is particularly effective.

The range of 3500:1 to 1:1 applies with regard to the determining weight ratios of the compounds II to III in the compositions according to the invention. The combination ratio in the range of 1000:1 to 1:1 is especially suitable for inducing the synergistic effect, and within these limits, the range of 500:1 to 1:1 is particularly effective.

Instead of being used as component in the compositions according to the invention, the inventive active-substance combination can also be used on its own. The proportion of the active-substance combination in the compositions according to the invention is 1 to 90% by weight, used together with 99 to 10% by weight of carriers and formulation auxiliaries.

The invention on which the compositions according to the invention are based is further illustrated by the following Examples. The biocidal activity of the active-substance combination is determined by means of the topical application method, and the potentiation effect is ascertained therefrom.

EXAMPLE 1

Forty flies (*Musca domestica* ♀ ♀) of a homogeneous population of the highly-resistant strain R-300 were dorsally treated by application in each case of 1 μl of an acetonic active-substance solution per ♀ fly. Ten individuals were placed together with a cotton wool pad soaked with hydromel into each of a number of Petri dishes (9 cm in diameter) at room temperature. An evaluation was made after 24 hours by ascertaining the percentage mortality rate. This procedure was carried out separately for each individual active-substance component and combinations thereof. By application of a logarithmically graduated concentration series, there were obtained increasing mortality values from which, with the Probit Analysis according to Finney[1], a dose-mortality straight line was calculated. The $LD_{50}$ values were determined in this manner.

[1] Finney D. J. 1952, Probit Analysis, 2nd Ed. Cambridge Univ. Press.

Evaluation

On the basis of these values, the potentiation rate (PR) was ascertained as a measure of the occurring synergism by means of the Cotox formula[2]. The potentiation rate (PR) is given from the following quotient:

$$PR = \frac{\widehat{LD_{50}}}{LD_{50}}$$

In this quotient, $LD_{50}$ represents the value of the active-substance combination measured in the toxicological test, whilst $\widehat{LD_{50}}$ denotes the expected value of the combination which is obtained by the following equation:

$$\widehat{LD_{50}} = \frac{1}{\frac{\mu A}{LD_{50}A} + \frac{\mu B}{LD_{50}B}}$$

The values μA and μB signify the proportion of the respective mixture component in the total mixture.
PR values of >1 indicate potentiation between the mixture components.

[2] Banki L. 1978, Bioassay of Pesticides in the Laboratory Research and Quality Control, p. 313, Akadémia Kiadó, Budapest.

Results

TABLE 1

| Active substance or active-substance mixture | Weight ratio of the mixture | $LD_{50}$ ng/♀ * calculated | found | Cotox coefficient |
|---|---|---|---|---|
| comp. I | — | — | 7509 | — |
| comp. II | — | — | 14527 | — |
| comp. III | — | — | 51.6 | — |
| comp. I/ | 1000:1 | 6587 | 2567 | 2.6 |
| comp. III | 145:1 | 3759 | 1037 | 3.6 |
|  | 30:1 | 1344 | 467 | 2.9 |
| comp. II/ | 1600:1 | 12300 | 6133 | 2.0 |
| comp. III | 280:1 | 7254 | 2654 | 2.7 |
|  | 60:1 | 2650 | 1150 | 2.3 |

*Musca domestica, strain R 300 (highly-resistant)

The mutual potentiation of two active substances can also be represented graphically according to Loewe and Muischnek[1]. In this case, the $LD_{50}$ values of any given mixture ratios are ascertained by means of an isobole, that is, a curve of equal toxic effect. With additive effect of the combination components, all $LD_{50}$ values move along a straight line. When potentiation occurs, however, this curve deviates in the form of a hyperbola from the straight line, the deviation increasing with the degree of potentiation.

[1] Loewe, S. and H. Muischnek, 1926, Über Kombinationswirkungen (Combination Effects), Arch. exp. Path. Pharmak. 114, 313–326.

According to Table 1, the mixture ratios of compound I/compound III=145:1 and of compound II/compound III=280:1 constitute preferred embodiments of the present invention.

The active-substance combinations on which the compositions according to the invention are based are used according to the invention together with suitable carriers and/or additives. Suitable carriers and additives are solid or liquid and correspond to the substances common in formulation practice, such as natural or regenerated substances, solvents, dispersing agents, wetting agents, adhesives, thickeners and/or binders.

For application, the active-substance combinations are processed according to the invention into the form of dusts, emulsion concentrates, granulates, dispersions, aerosols, sprays, solutions or suspensions. Furthermore, aqueous preparations or concentrates of the active-substance combinations are used according to the invention for cattle dips and spray races, and also in the pour-on method, the hand-spray method and the hand-dressing method.

The compositions according to the invention are produced by intimate mixing and/or grinding of the active-substance combinations with suitable carriers, optionally with the addition of dispersing agents or solvents which are inert to the active substances. The active-substance combinations can be obtained and used in the following forms:

solid preparations: dusts, scattering agents and granulates;

liquid preparations:
(a) water-dispersible concentrates of active-substance combinations: wettable powders, pastes and emulsions;
(b) solutions.

The content of an active-substance combination in the preparations described above is between 1 and 90% by wt.

EXAMPLE 2

Emulsion concentrate 20 parts by weight of an active-substance combination are dissolved in 70 parts by weight of xylene, and to this solution are added 10 parts by weight of an emulsifier consisting of a mixture of an arylphenyl polyglycol ether and the calcium salt of dodecylbenzenesulfonic acid.

Water can be added in any proportion to the emulsion concentrate to form a milky emulsion.

EXAMPLE 3

Emulsion concentrate 5 to a maximum of 50 parts by wt. of an active-substance combination are dissolved at room temperature, with stirring, in 30 parts by weight of dibutyl phthalate, 10 parts by weight of solvent 200 (low-viscous, highly aromatic petroleum distillate), 15 to 35 parts by weight of Dutrex 238 FC (viscous highly aromatic petroleum distillate), and to this solution are added 10 parts by weight of an emulsifier mixture consisting of castor oil polyglycol ether and the calcium salt of dodecylbenzenesulfonic acid.

Milky emulsions are formed by adding water to the emulsion concentrate obtained.

EXAMPLE 4

Wettable powder 5 to 50 parts by weight of an active-substance combination are vigorously mixed, in a mixing apparatus, with 5 parts by weight of an absorbent carrier (amorphous silicic acid or Wessalon S) and 55 to 80 parts by weight of a carrier (bolus alba or kaolin B 24), and a dispersing agent mixture consisting of 5 parts by weight of a sodium lauryl sulfonate, and 5 parts by weight of an alkyl-aryl-polyglycol ether.

This mixture is ground in a dowelled disk mill or air-jet mill to a particle size of 5–15 μm. The wettable powder thus obtained gives a good suspension in water.

EXAMPLE 5

Dust 5 parts by weight of an active-substance combination are thoroughly mixed with 2 parts by weight of a precipitated silicic acid, and 92 parts of weight of talcum.

The compositions according to the invention are particularly suitable for controlling stored-food pests and granary pests, because these compositions satisfy to a great extent the requirements necessary for the protection of stored foodstuffs. They are thus distinguished by having the following properties: low lethal minimum concentration for pests (especially for resistant forms), low toxicity to humans and to productive animals, uniform duration of effect over several months, and no residue problems.

By virtue of these properties, it is possible to successfully control with the compositions according to the invention the following typical stored-food pests, granary pests and other storehouse pests:

| | |
|---|---|
| Oryzaephilus surinamensis | saw-toothed grain beetle |
| Trogoderma granarium | khapra beetle |
| Lasioderma serricorne | cigarette beetle |
| Chryptolestes ferrugineus | flat grain beetle |
| Stegobium paniceum | bread beetle |
| Necrobia rufipes | copra beetle |
| Anthrenus vorax | carpet beetle |

-continued

| | |
|---|---|
| Sitophilus granarius | grain weevil |
| Sitophilus oryzae | rice weevil |
| Sitophilus zea mais | maize weevil |
| Rhizopertha dominica | lesser grain borer |
| Acanthoselides obtecus | common bean weevil |
| Sitotroga cerealella | grain moth |
| Nemapagon granellus | European grain moth |
| Tyrophagus putrescentiae | foodstuff and feed mite |
| Acarus siro | flour mite |
| Ephestia kuehniella | flour moth |
| Araeocerus fasciculatus | coffee-bean weevil |
| Carpophilus hemipterus | dried fruit beetle |
| Tenebrio molitor | yellow mealworm |
| Tribolium castaneum | red flour beetle |
| Tribolium destructor | black-brown mealworm |
| Tribolium confusum | confused flour beetle; |
| and also cockroaches: | |
| Phyllodromia germanica | German cockroach |
| Periplaneta americana | American cockroach |
| Blatta orientalis | Russian cockroach |

A further important aspect of the present invention is that the compositions of the invention can be successfully used also against hygiene pests, such as flies and fly larvae, as well as against mosquitoes and mosquito larvae; and they thus make a significant contribution towards the preservation of the health of humans and animals by preventing the spread of disease. Furthermore, the yield of productive animals is considerably improved by the use of the compositions according to the invention in agriculture.

What is claimed is:

1. A composition for control of insects and acarids which comprises at least an insecticidally and acaricidally effective amount of a mixture of (i) methyl 3-hydroxymethacrylate-O,O-dimethylthionophosphate and (ii) alpha-cyano-3-phenoxybenzyl 3-(2,2-dichlorovinyl)-2,2-dimethylcyclopropane carboxylate in a weight ratio of from about 3500:1 to about 10:1 in a carrier therefor.

2. A method of controlling insects and acarids which comprises applying thereto or to a habitat thereof an insecticidally and acaricidally effective amount of a mixture of (i) methyl 3-hydroxymethacrylate-O,O-dimethylthionophosphate and (ii) alpha-cyano-3-phenoxybenzyl 3-(2,2-dichlorovinyl)-2,2-dimethylcyclopropane carboxylate in a weight ratio of from about 3500:1 to about 10:1.

* * * * *